(12) United States Patent
Georgeson et al.

(10) Patent No.: US 10,562,284 B2
(45) Date of Patent: Feb. 18, 2020

(54) SELF-INDICATING BACKING PAPER AND METHODS FOR USE

(71) Applicant: The Boeing Company, Chicago, IL (US)

(72) Inventors: Gary E. Georgeson, Seattle, WA (US); Xiaoxi Wang, Mukilteo, WA (US); Richard Henry Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 237 days.

(21) Appl. No.: 15/397,169

(22) Filed: Jan. 3, 2017

(65) Prior Publication Data
US 2018/0186137 A1 Jul. 5, 2018

(51) Int. Cl.
| | | |
|---|---|---|
| *B32B 41/00* | (2006.01) | |
| *B32B 29/00* | (2006.01) | |
| *G01N 29/04* | (2006.01) | |
| *G01N 29/22* | (2006.01) | |
| *B29C 70/30* | (2006.01) | |
| *B29C 37/00* | (2006.01) | |
| *B29C 70/54* | (2006.01) | |
| *B32B 37/18* | (2006.01) | |
| *B32B 38/10* | (2006.01) | |
| *B32B 38/00* | (2006.01) | |
| *B29L 7/00* | (2006.01) | |
| *B29L 9/00* | (2006.01) | |

(Continued)

(52) U.S. Cl.
CPC ........ *B32B 29/002* (2013.01); *B29C 37/0075* (2013.01); *B29C 70/30* (2013.01); *B29C 70/54* (2013.01); *G01N 29/04* (2013.01); *G01N 29/043* (2013.01); *G01N 29/225* (2013.01); *B29C 44/3484* (2013.01); *B29K 2105/24* (2013.01); *B29L 2007/00* (2013.01); *B29L 2009/00* (2013.01); *B32B 37/18* (2013.01); *B32B 38/0036* (2013.01); *B32B 38/10* (2013.01); *B32B 41/00* (2013.01); *B32B 2260/00* (2013.01); *G01N 2291/0231* (2013.01); *G01N 2291/106* (2013.01)

(58) Field of Classification Search
CPC ....... B32B 29/002; B32B 38/10; B32B 37/18; B32B 41/00; B32B 38/0036; G01N 29/043; G01N 29/225; G01N 29/04; G01N 2291/106; G01N 2291/0231; B29C 70/30; B29C 53/32; B29C 44/02
USPC .......................... 156/64, 350, 351, 378, 379
See application file for complete search history.

(56) References Cited

U.S. PATENT DOCUMENTS

| | | | | |
|---|---|---|---|---|
| 3,864,181 A | * | 2/1975 | Wolinski | C08J 9/04 156/79 |
| 4,163,824 A | * | 8/1979 | Saidla | B29C 44/02 428/317.9 |

(Continued)

*Primary Examiner* — Michael N Orlando
*Assistant Examiner* — Joshel Rivera
(74) *Attorney, Agent, or Firm* — McDonnell Boehnen Hulbert & Berghoff LLP (57) ABSTRACT

Example systems and methods are described including backing paper for use with uncured pre-impregnated material. An example system includes a backing paper having a first surface and a second surface. The system also includes a coating material positioned on the first surface of the backing paper. A blowing agent is encapsulated within the coating material.

20 Claims, 7 Drawing Sheets

(51) Int. Cl.
   *B29C 44/34* (2006.01)
   *B29K 105/24* (2006.01)

(56) References Cited

U.S. PATENT DOCUMENTS

| | | | | |
|---|---|---|---|---|
| 4,844,849 | A * | 7/1989 | Miller | B29C 44/00 264/46.4 |
| 5,954,917 | A * | 9/1999 | Jackson | B29C 70/342 156/433 |
| 2007/0100582 | A1* | 5/2007 | Griess | G01M 5/0033 702/183 |
| 2009/0302509 | A1* | 12/2009 | Debiasi | B29C 44/06 264/511 |

* cited by examiner

SELF-INDICATING BACKING PAPER AND METHODS FOR USE

FIELD

The present disclosure relates generally to a backing paper for use in preparing, storing, and transporting uncured pre-impregnated material, and more particularly, to a backing paper that reduces difficult-to-detect foreign object debris (FOD) cured in a layered composite.

BACKGROUND

Backing paper is used to separate uncured pre-impregnated material used to fabricate composite structures. The backing paper operates to maintain separation between layers of pre-impregnated material as it is rolled up so that the pre-impregnated material does not stick to itself during transportation and storage. The combined pre-impregnated material and backing paper roll may then be unrolled during fabrication by automated or manual means and the backing paper can be removed thrown away as the pre-impregnated material is applied to a second material to create a layered material. Such backing paper typically includes a coating material that enables the backing paper to be more easily removed from the uncured pre-impregnated material. A problem that may arise in the process is that a portion of the backing paper can sometimes remain attached to the pre-impregnated material and become sandwiched in the layered material. This produces FOD that creates a weak region or defect in the layered material. Such backing paper FOD can be very difficult to detect using typical non-destructive examination (NDE) methods, such as ultrasound testing, infrared thermography, or x-ray testing.

One reason that detection is difficult is because the backing paper may be of similar ultrasonic impedance as the layered material, and may not create as strong a reflection as an air void or delamination. Similarly, the backing paper may not create a strong thermal transport difference for infrared thermography to detect. If a section of backing paper remains on the uncured pre-impregnated material, traditional non-destructive examination may be even more likely to miss the backing paper since the area with the backing paper will appear uniformly good. Such backing paper remaining between layers of a layered material may cause failure of the component, if it is not detected. Therefore, an improved backing paper that is easier to detect under traditional non-destructive examination may be desirable.

SUMMARY

In one example, a system is described. The system includes a backing paper having a first surface and a second surface. The system also includes a coating material positioned on the first surface of the backing paper. A blowing agent is encapsulated within the coating material.

In another example, a method is described. The method includes applying a first surface of a backing paper to a first surface of an uncured pre-impregnated material. The first surface of the backing paper includes a coating material with a blowing agent encapsulated within the coating material. The method also includes rolling the backing paper and the pre-impregnated material simultaneously such that a second surface of the uncured pre-impregnated material contacts a second surface of the backing paper.

In still another example, another method is described. The method includes removing a backing paper from a first surface of an uncured pre-impregnated material. A first surface of the backing paper includes a coating material with a blowing agent encapsulated within the coating material. The method also includes placing a second material on the first surface of the uncured pre-impregnated material. The method also includes curing the pre-impregnated material and the second material at a curing temperature so that the pre-impregnated material adheres to the second material to create a layered material. The method also includes positioning the layered material in a field of view of a transducer. The method also includes generating, using the transducer, a plurality of ultrasonic waves. The method also includes receiving ultrasonic waves reflected from and generated in the layered material. And the method includes analyzing, using a computing device, signals indicative of the ultrasonic waves to determine at least one property of the layered material.

The features, functions, and advantages that have been discussed can be achieved independently in various embodiments or may be combined in yet other embodiments further details of which can be seen with reference to the following description and figures.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying figures, wherein:

DETAILED DESCRIPTION

Disclosed embodiments will now be described more fully hereinafter with reference to the accompanying figures, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

Within examples, a system is described including a backing paper for application with uncured pre-impregnated materials. In some examples, the systems and methods described herein may facilitate non-contact nondestructive testing and characterization of materials and structures using ultrasound waves, as one example. For instance, the systems and methods described herein may enable an inspector to evaluate a layered object and characterize any defects in the object.

As discussed above, traditionally a backing paper is used to separate uncured pre-impregnated material used to fabricate composite structures. The backing paper allows the pre-impregnated material to be rolled up for transportation and storage. The pre-impregnated material may then be unrolled during fabrication by automated or manual means, and the backing paper may be removed from the pre-impregnated material and thrown away before the pre-impregnated material is applied to a second material to thereby create a layered composite structure. At least one side of the backing paper may include a coating material that enables the backing paper to be more easily removed from the uncured pre-impregnated material. A problem that may arise in this process is that parts of the backing paper may sometimes remain attached to the pre-impregnated material and become sandwiched in the layered composite structure. This produces foreign object debris (FOD) that creates a weak region or defect in the layered material. Such backing paper FOD can be very difficult to detect using typical non-destructive examination (NDE) methods, such as ultrasound testing.

Within examples disclosed herein, a system includes a backing paper having a first surface and a second surface. The system also includes a coating material positioned on the first surface of the backing paper, and a blowing agent encapsulated within the coating material. By encapsulating a blowing agent in the coating material of the backing paper, the process of curing the pre-impregnated material causes the blowing agent of any backing paper accidentally left behind between the pre-impregnated material and the second material to activate. The activated blowing agent will create voids which are then more easily detected by typical NDE methods, such as ultrasound. As such, any backing paper that remains attached between layers of pre-impregnated material may be more easily detected using current NDE testing methods, without the need for more time-consuming or costly detection measures.

Various other features of the example systems discussed above, as well as methods for evaluating an object using these systems, are also described hereinafter with reference to the accompanying figures.

Figure 1:
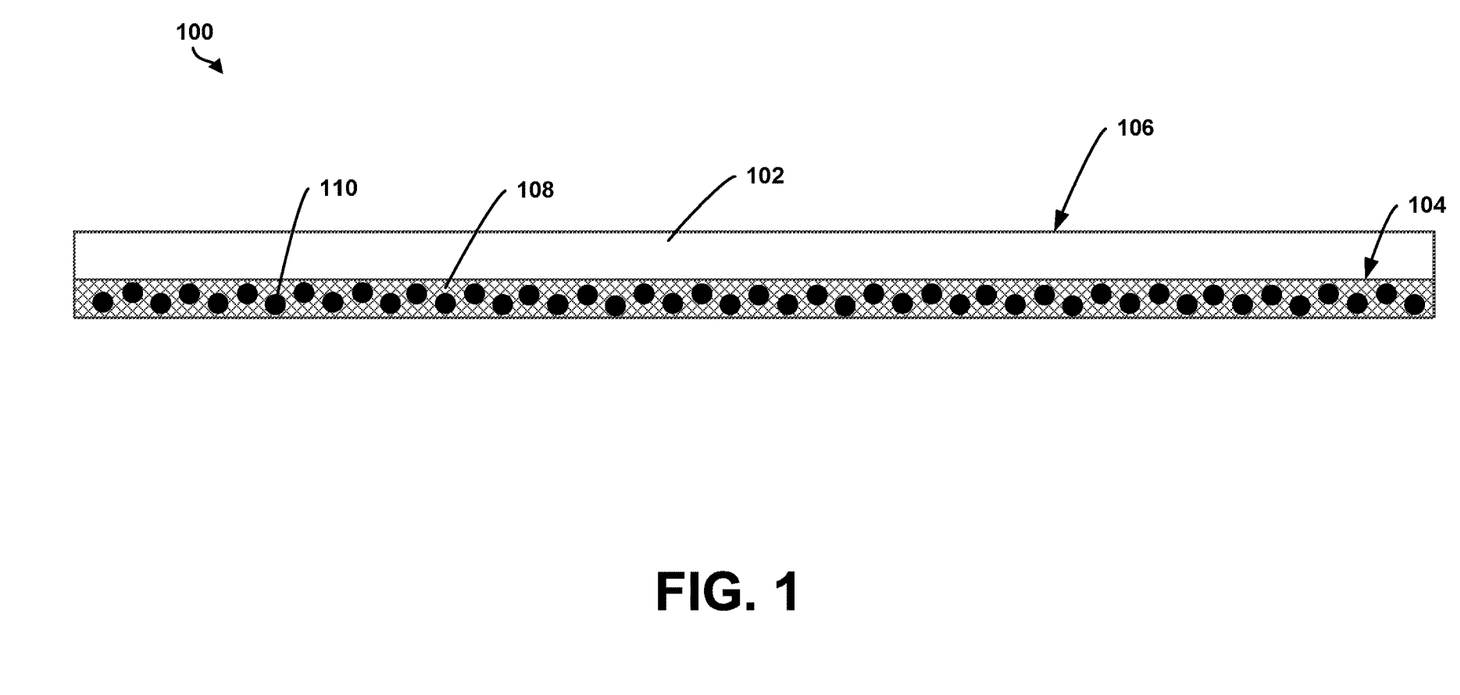
FIG. 1 is a conceptual illustration of an example system, according to an example embodiment.

Referring now to the figures, FIG. 1 illustrates a system 100 according to an example embodiment. As shown in FIG. 1, the system 100 may include a backing paper 102 having a first surface 104 and a second surface 106. The system 100 may further include a coating material 108 positioned on the first surface 104 of the backing paper 102. In one example, the coating material 108 may include any material(s) designed to enable the backing paper 102 to be more easily removed from another material to which the backing paper 102 is coupled, such as an uncured pre-impregnated material, as discussed in more detail below.

The backing paper 102 may comprise a cellulose paper, polymeric sheet including polyamide, polyether-terephthalate, polyethersulphones, acrylate polymers, polyesters, polyethylene or copolymers thereof. The coating material 108 may comprise a silicone material to reduce the adhesive force between the backing paper 102 and an uncured pre-impregnated material onto which the backing paper 102 may be placed.

Further, the system 100 may include a blowing agent 110 encapsulated within the coating material 108. The blowing agent 110 is a substance which is capable of producing a cellular structure via a foaming process in a material that undergoes a hardening or phase transition, such as a pre-impregnated material. The cellular structure in a matrix reduces density, increasing thermal and acoustic insulation, while increasing relative stiffness of the original material. The blowing agent 110 may take various forms. In one example, the blowing agent 110 comprises a chemical blowing agent. In such an example, the chemical blowing agent is one of azodicarbonamide, benzene sulfonyl hydrazide, toluenesulfonyl-semicarbaside, 5-Phenyltetrazole, dinitrozopentamethylentetraamin, sodium bicarbonate, or citric acid. In chemical blowing agents, gaseous products and other by-products are formed by a chemical reaction(s), promoted by process or a reacting polymer's exothermic heat. Since the chemical blowing reaction occurs with low molecular weight compounds acting as the blowing gas, additional exothermic heat is also released. Once formed, the low molecular weight compounds will never revert to the original blowing agent(s), i.e. the reaction is irreversible.

In another example, the blowing agent 110 comprises a physical blowing agent. In such an example, the physical blowing agent is one of chlorofluorocarbons (CFCs), hydro-chlorofluorocarbons (HCFCs), hydrofluorocarbon (HFC), propane, isobutane, pentane, ethanol, carbon dioxide (CO2), or nitrogen (N2). These physical blowing agents may be injected as gases or supercritical fluids into small thermoplastic materials, and when the temperature of the thermoplastic material is raised the gases or supercritical fluids expand to create voids in the coating material 108.

In yet another example, the blowing agent 110 comprises a mixed physical/chemical blowing agent. In such an example, both the chemical and physical blowing agents may be used in tandem to balance each other out with respect to thermal energy being released and/or absorbed, thereby minimizing temperature rise. Excessive exothermic heat due to high loading of a physical blowing agent may cause thermal degradation of the coating material 108 and/or the backing paper 102. Therefore, a mixed physical/chemical blowing agent may prevent such degradation.

The blowing agent 110 may be encapsulated in the coating material 108 by pre-mixing the blowing agent into a liquid coating material 108 before applying the liquid coating material is applied to the backing paper 102. In one example, such a liquid coating material 108 may be sprayed on the backing paper 102. In one example, a weight of the blowing agent 110 encapsulated in the coating material 108 may only comprise about 0.1% to about 3% of the combined weight of the blowing agent 110 and coating material 108. As described above, the blowing agent 110 may comprise a particle into which the blowing agent 110 is positioned. The size of such particles may be controlled in a wide range, for example about 3 μm to about 50 μm. The particles may be dispersed into the liquid coating material 108 before applying the liquid coating material 108 to the backing paper 102, and the blowing agent 110 is thereby encapsulated in the coating material 108 without affecting the surface quality of the coating material 108. The coating material may then be cured on the backing paper 102 to form a finished product that can then be applied to another material, as discussed below in relation to FIG. 2. In such a manner, the blowing agent 110 can be sealed reliably between the coating material 108 with controlled risks of contamination.

In another embodiment, the backing paper 102 may comprise an uncoated plastic film, such as polypropylene film with low surface energy. In such an embodiment, the backing paper 102 and the coating material 108 including the blowing agent 110 don't have to be two separate layers. Instead, the blowing agent 110 can be mixed into the uncoated plastic film during a film extrusion process (as long as the activation temperature of the blowing agent 110 is lower than the extrusion temperature). In this case, the blowing agent 110 will be uniformly dispersed in the film both in plane and in thickness.

Figure 2:
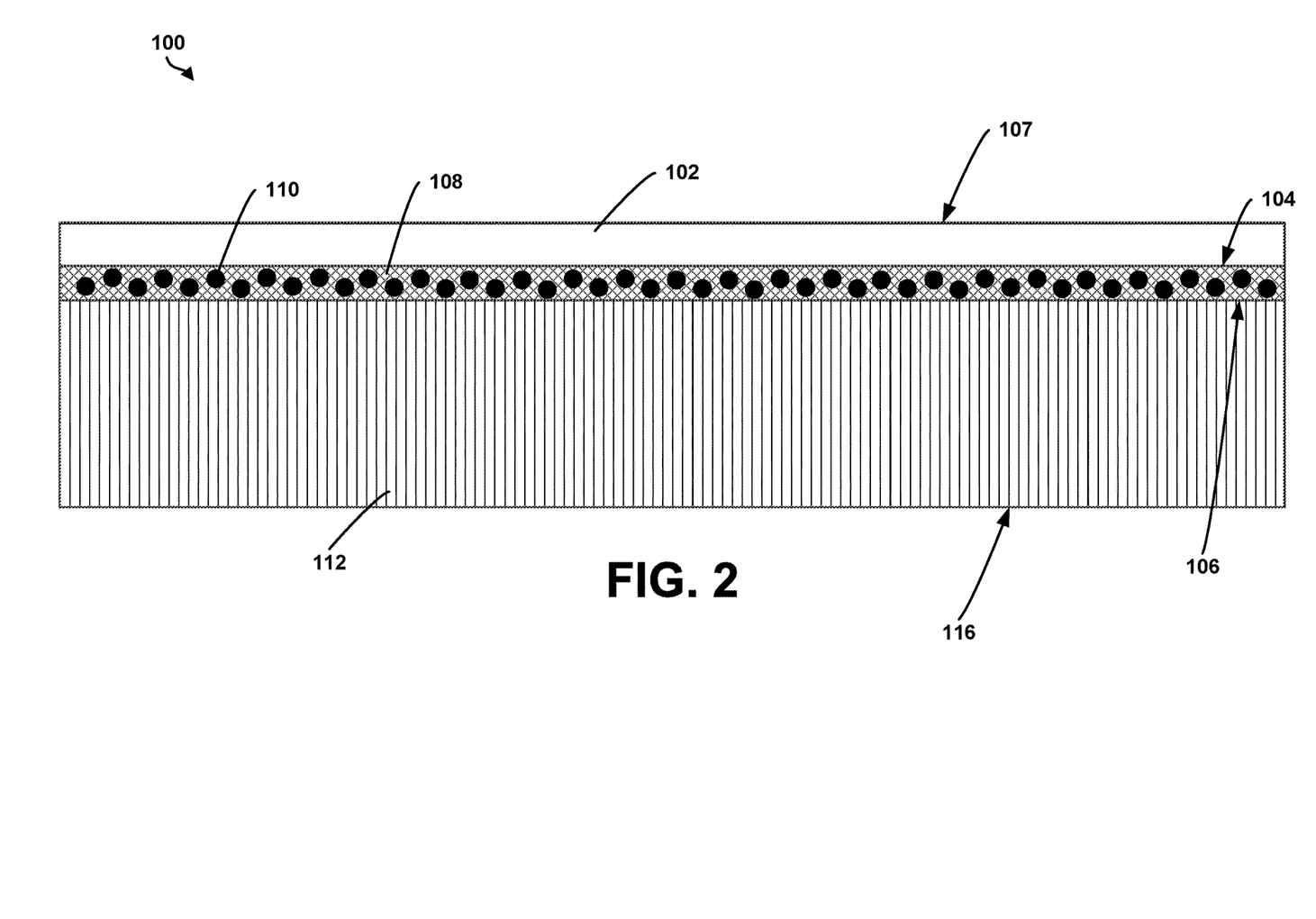
FIG. 2 is a conceptual illustration of another example system, according to an example embodiment.

FIG. 2 illustrates another example embodiment of system 100. As shown in FIG. 2, the system 100 further includes an uncured pre-impregnated material 112 temporarily coupled to the coating material 108. However, the adhesion between the coating material 108 and the backing paper 102 is much greater than any adhesion that would occur between the coating material 108 and the pre-impregnated material 112. The uncured pre-impregnated material may be a reinforcing tape or fabric, in one example. In another example, the uncured pre-impregnated material may be a composite material. The uncured pre-impregnated material can include a plurality of fibers such as graphite fibers that are embedded within a matrix material, such as a polymer, e.g., an epoxy or phenolic. The uncured pre-impregnated material could be unidirectional or woven depending on a degree of reinforcement desired.

As described above, the backing paper 102 operates to maintain separation between layers of pre-impregnated material 112 as it is rolled up so that the pre-impregnated material 112 does not stick to itself during transportation and storage. The temporary coupling of the uncured pre-impregnated material 112 to the coating material 108 enables the backing paper 102 to be removed from the uncured pre-impregnated material 112 before curing. The uncured pre-impregnated material 112 has a curing temperature, and the blowing agent 110 has an activation temperature, above which the blowing agent 110 produces a cellular structure in the coating material 108. The activation temperature of the blowing agent 110 is less than the curing temperature of the uncured pre-impregnated material 112. Further, as discussed above, the coating material 108 has a curing temperature as well, and the activation temperature of the blowing agent 110 is greater than the curing temperature of the coating material. In one example, the activation temperature of the blowing agent 110 has a range from about 200° F. to about 450° F.

Figure 3A:
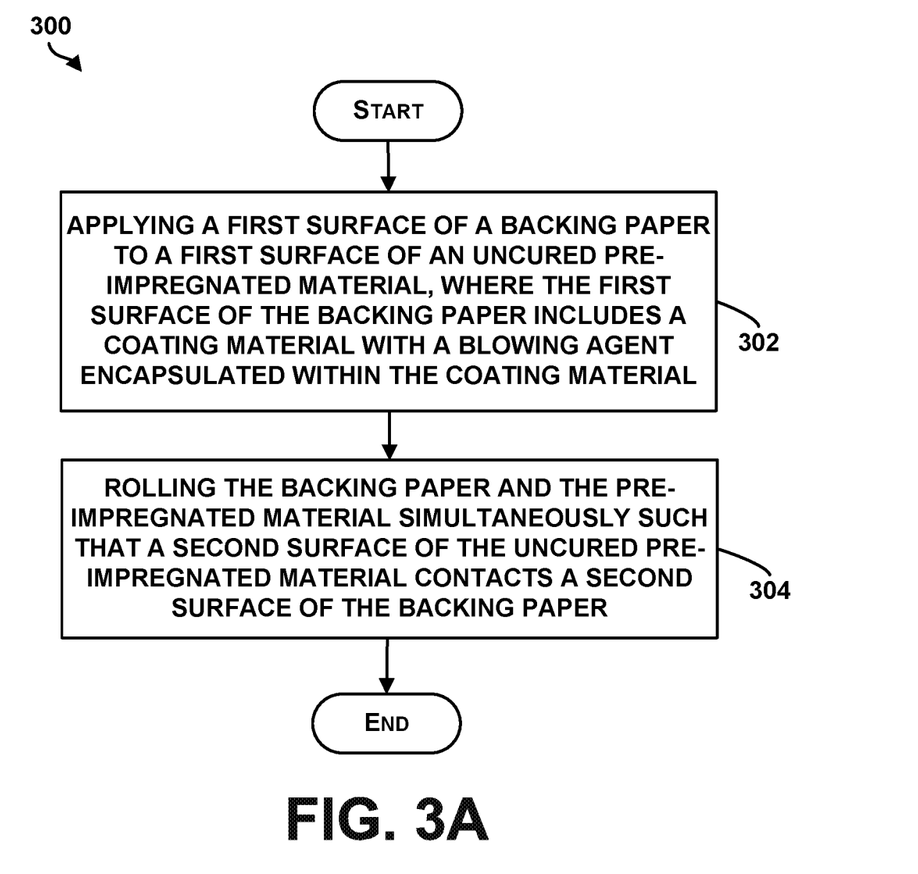
FIG. 3A is a flowchart of an example method, according to an example embodiment.

FIG. 3A is a flowchart of an example method according to an example embodiment. Method 300 shown in FIG. 3A presents an example of a method that could be used during formation of the system 100 as shown in FIGS. 1-2, for example. Further, devices or systems may be used or configured to perform logical functions presented in FIG. 3A. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. The computer readable medium may include non-transitory computer readable medium or memory, for example, such as computer readable media that stores data for short periods of time like register memory, processor cache, and RAM. The computer readable media may also be any other volatile or non-volatile storage systems. The computer readable medium may be considered a tangible computer readable storage medium, for example.

In some examples, the functions described in FIG. 3A and the other methods disclosed herein may be performed manually. In another example, the functions described in FIG. 3A the other methods disclosed herein may be performed at least in part by a robotic device or some other automated manner. Method 300 may include one or more operations, functions, or actions as illustrated by one or more of blocks 302-304. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. Alternative implementations are included within the scope of the examples of the present disclosure in which functions may be executed out of order from that shown or discussed, including substantially concurrent or in reverse order, depending on the functionality involved, as would be understood by those reasonably skilled in the art.

Initially, at block 302, the method 300 includes applying a first surface 104 of a backing paper 102 to a first surface 106 of an uncured pre-impregnated material 112. As discussed above in relation to FIGS. 1-2, the first surface 104 of the backing paper 102 includes a coating material 108 with a blowing agent 110 encapsulated within the coating material 108. The backing paper 102 is configured to cover substantially all of the first surface 106 of the uncured pre-impregnated material 112.

At block 304, the method 300 includes rolling the backing paper 102 and the pre-impregnated material 112 simultaneously such that a second surface 116 of the uncured pre-impregnated material 112 contacts a second surface of the backing paper 107. The rolled up backing paper 102 protects the uncured pre-impregnated material 112 during transportation and storage. In various examples, as discussed above, applying the first surface 104 of the backing paper 102 to the first surface 106 of the uncured pre-impregnated material 112 comprises applying a backing paper 102 where the blowing agent 110 of the coating material 108 comprises one of a chemical blowing agent, a physical blowing agent, or a mixed physical/chemical blowing agent.

Figure 3B:
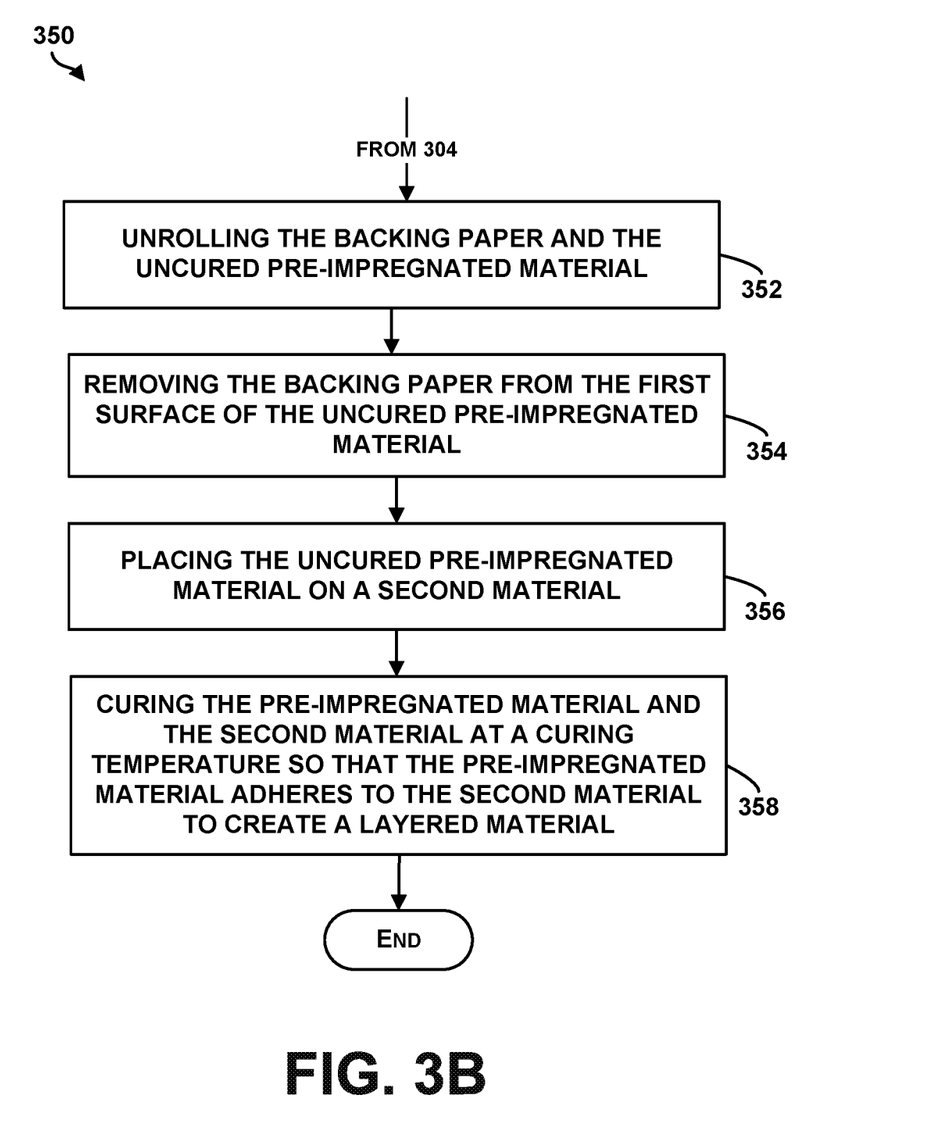
FIG. 3B is a flowchart illustrating an example method, which is a continuation of the method shown in FIG. 3A, according to an example embodiment.
Figure 4:
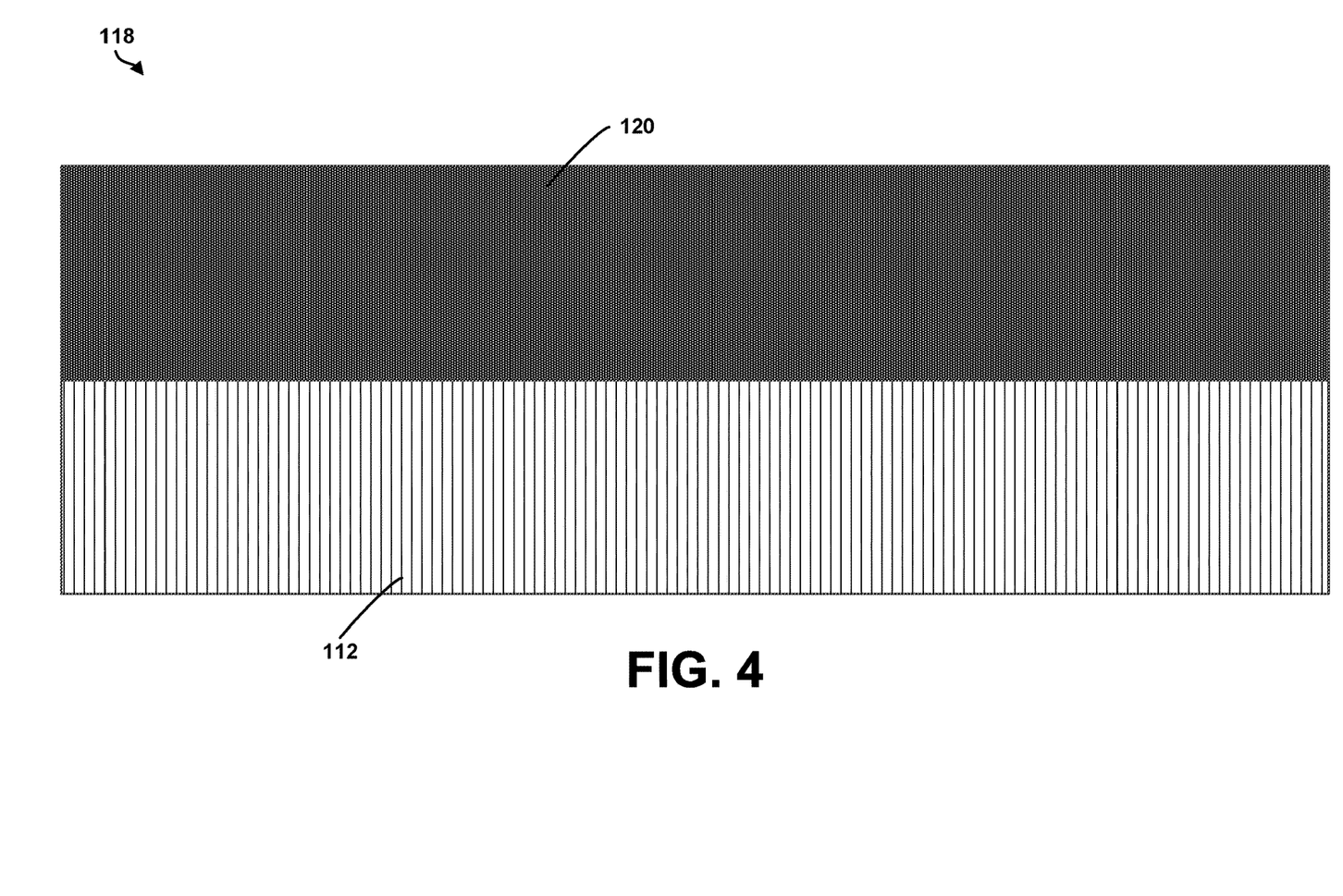
FIG. 4 is a conceptual illustration of an example layered material, according to an example embodiment.

FIG. 3B is a flowchart illustrating method 350, which is a continuation of method 300 shown in FIG. 3A. Method 350 shown in FIG. 3B presents an example of a method that could be used during formation of the layered material 118 as shown in FIG. 4, for example. Further, devices or systems may be used or configured to perform logical functions presented in FIG. 3B. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 350 may include one or more operations, functions, or actions as illustrated by one or more of blocks 352-358. Also, the various blocks may be combined into fewer blocks, divided into additional blocks, and/or removed based upon the desired implementation.

Initially, at block 352, the method 350 includes unrolling the backing paper 102 and the uncured pre-impregnated material 112. Next, at block 354, the method 350 includes removing the backing paper 102 from the first surface 106 of the uncured pre-impregnated material 112. As discussed above, the coating material 108 may comprise a silicone material to reduce the adhesive force between the backing paper 102 and the uncured pre-impregnated material 112, thereby easing removal of the backing paper 102 from the unrolled uncured pre-impregnated material 112. In addition, as discussed above, the adhesion between the coating material 108 and the backing paper 102 is much greater than any adhesion that would occur between the coating material 108 and the pre-impregnated material 112. As such, when the backing paper 102 is removed from the uncured pre-impregnated material 112, no blowing agent 110 is left behind on the first surface 106 of the uncured pre-impregnated material 112.

At block 356, the method 350 includes placing the uncured pre-impregnated material 112 on a second material 120. In one example, the second material 120 may be a second layer of uncured pre-impregnated material. In another example, the second material 120 may be a layered material with a plurality of uncured pre-impregnated layers. Other examples are possible as well.

At block 358, the method 350 includes curing the pre-impregnated material 112 and the second material 120 at a curing temperature so that the pre-impregnated material 112 adheres to the second material 120 to create a layered material 118. An example layered material 118 is shown in FIG. 4, including the pre-impregnated material 112 and the second material 120. As discussed above, the pre-impregnated material 112 may include composite fibers positioned in a matrix material, such as epoxy. The fibers may take the form of a weave and the matrix may be used to bond them together and to other components during curing. In one example, curing the pre-impregnated material 112 comprises curing the pre-impregnated material at a temperature above an activation temperature of the blowing agent, such that the blowing agent 110 of any backing paper 102 sandwiched between the pre-impregnated material 112 and the second material 120 is activated when the pre-impregnated material 112 is cured. In another example, as discussed above in relation to FIGS. 1-2, curing the pre-impregnated material 112 at the temperature above the activation temperature of the blowing agent 110 comprises curing the pre-impregnated material 112 at the activation temperature of the blowing agent 110 in a range from about 200° F. to about 450° F.

Figure 5:
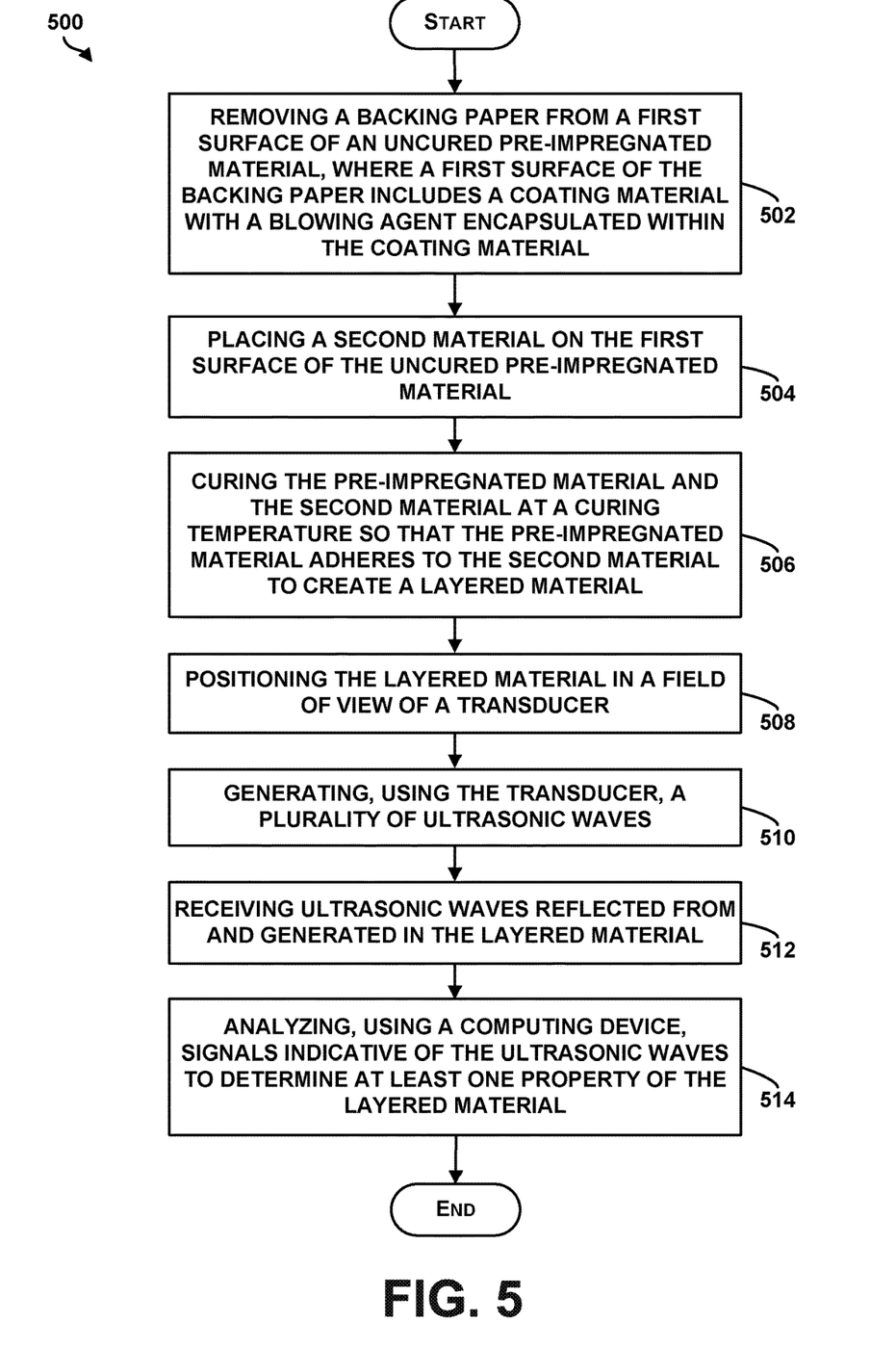
FIG. 5 is a flowchart of an example method for nondestructive testing, according to an example embodiment.

FIG. 5 is a flowchart of another example method for nondestructive testing according to an example embodiment. Method 500 shown in FIG. 5 presents an example of a method that could be used for nondestructive testing of a layered material, using the system 600 shown in FIG. 6, for example. Further, devices or systems may be used or configured to perform logical functions presented in FIG. 6. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 230 may include one or more operations, functions, or actions as illustrated by one or more of blocks 232-246. Also, the various blocks may be combined into fewer blocks, divided into additional blocks, and/or removed based upon the desired implementation.

Initially, at block 502, the method 500 includes removing a backing paper from a first surface of an uncured pre-impregnated material. As discussed above in relation to FIGS. 1-2, the first surface of the backing paper 102 includes a coating material 108 with a blowing agent 110 encapsulated within the coating material 108. In one example, as discussed above, removing the backing paper 102 from the first surface 106 of the uncured pre-impregnated material 112 comprises removing a backing paper 102 where the blowing agent 110 of the coating material 108 comprises one of a chemical blowing agent, a physical blowing agent, or a mixed physical/chemical blowing agent.

At block 504, the method 500 includes placing a second material 120 on the first surface 106 of the uncured pre-impregnated material 112. FIG. 4 illustrates the second material 120 positioned on the first surface of the uncured pre-impregnated material 112. In one example, the second material 120 may be a second layer of uncured pre-impregnated material. In another example, the second material 120 may be a layered material with a plurality of uncured pre-impregnated layers. Other examples are possible as well.

At block 506, the method 500 includes curing the pre-impregnated material 112 and the second material 120 at a curing temperature so that the pre-impregnated material 112 adheres to the second material 120 to create a layered material 118.

Figure 6:
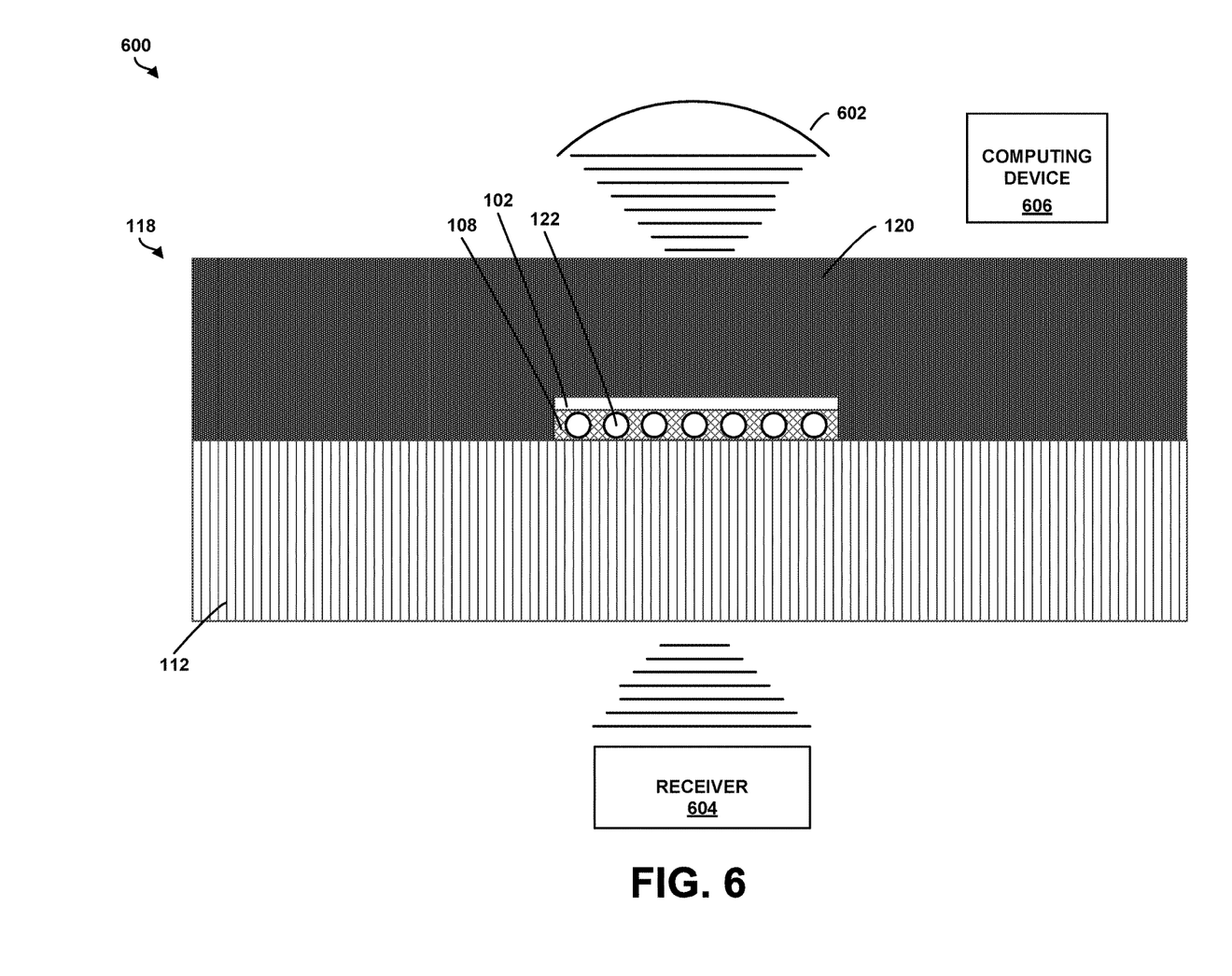
FIG. 6 is a conceptual illustration of an example system for nondestructive testing, according to an example embodiment.

At block 508, the method 500 includes positioning the layered material 118 in a field of view of a transducer. FIG. 6 illustrates an example system 600 including a transducer 602, a receiver 604, and a computing device 606, which may be coupled together by a system bus, network, or other connection mechanism (not shown). In one, the single ultrasonic transducer 602 may be replaced by a transducer array. Thus, although the system 600 of FIG. 6 is described as including a single ultrasonic transducer 602, the example is not meant to be limiting. In one example, positioning the layered material in the field of view of the transducer may involve directing (e.g., electronically or mechanically steering) the ultrasound waves emitted by the transducer 602. Additionally or alternatively, positioning the layered material 118 in the field of view of the transducer 602 may involve focusing the transducer 602 on the surface of the layered material 118. In some examples, an operator or a robotic system may position the transducer 602 within a predetermined distance of the layered material 118. For instance, the operator or robotic system may move the transducer 602 such that it is focused on the surface of the layered material 118.

Referring back to FIG. 5, at block 510, the method 500 includes generating, using the transducer 602, a plurality of ultrasonic waves. In practice, the ultrasound waves emitted by the transducer 602 may propagate throughout the layered material 118 in a variety of modes, such as longitudinal, shear, surface, and others. The propagation throughout the layered material 118 may, in turn, generate secondary ultrasound and/or acoustic waves.

At block 512, the method 500 includes receiving ultrasonic waves reflected from and generated in the layered material 118. The receiver 604 may be configured to receive the ultrasound and/or acoustic waves reflected from and generated in the layered material 118 in various places around the layered material 118. In some examples, the receiver 604 may be an air-coupled receiver. The receiver 604 may, in turn, provide the received signals to the computing device 606. The receiver 604 may be located on a same side of the layered material 118 as the transducer 602 or an opposite side of the layered material 118.

The computing device 606 may function to control the transducer 602. For instance, the computing device 606 may energize the transducer 602 to emit ultrasound waves. As another example, the computing device 606 may direct and/or focus the transducer 602 to adjust a position of an interference field. The computing device 606 may also function to control the receiver 604 to process signals received from the receiver 604. The receiver 604 may operate at multiple frequencies simultaneously. Thus, the computing device 606 may be configured to process signals received from the receiver 604 in the time domain, the frequency domain, or both.

In one example, the computing device 606 may include one or more processors and one or more memories. The computing device 606 may be any type of device that can receive data and display information corresponding to or associated with the data. For example, the computing device 606 may be a mobile phone, a tablet, or a personal computer as examples.

Thus, the computing device 606 may include a display system comprising a processor and a display. The display may be, for example, an optical see-through display, an optical see-around display, or a video see-through display. The processor may receive data from the receiver 604, and configure the data for display on the display. Depending on the desired configuration, processor can be any type of processor including, but not limited to, a microprocessor, a microcontroller, a digital signal processor, or any combination thereof.

The computing device 606 may further include on-board data storage, such as memory coupled to the processor. The memory may store software that can be accessed and executed by the processor, for example. Further, processor may receive data from the receiver 604, and configure the data for storage in the memory. For example, the processor may receive ultrasound data from the receiver 604, and configure the data for storage in the memory. The memory can include any type of memory now known or later developed including but not limited to volatile memory (such as RAM), non-volatile memory (such as ROM, flash memory, etc.) or any combination thereof.

According to an example embodiment, the computing device 606 may include program instructions that are stored in the memory (and/or possibly in another data-storage medium) and executable by the processor to facilitate the various functions described herein. Although various components of the computing device 606 are shown as distributed components, it should be understood that any of such components may be physically integrated and/or distributed according to the desired configuration of the computing system.

At block 514, the method 500 includes analyzing, using a computing device, signals indicative of the ultrasonic waves to determine at least one property of the layered material 118. In one example, the computing device may be the computing device 606, as described above. In one example, as discussed above, curing the pre-impregnated material 112 comprises curing the pre-impregnated material 112 at a temperature above an activation temperature of the blowing agent 110, such that the blowing agent 110 of any backing paper 102 sandwiched between the pre-impregnated material 112 and the second material 102 is activated when the pre-impregnated material 112 is cured. In another example, as discussed above, curing the pre-impregnated material 112 at the temperature above the activation temperature of the blowing agent 110 comprises curing the pre-impregnated material 112 at the activation temperature of the blowing agent 110 in a range from about 200° F. to about 450° F.

In one example, the uncured pre-impregnated material 112 is a first uncured pre-impregnated material, and the method 500 further comprises placing a second uncured pre-impregnated material on the first uncured pre-impregnated material, and curing the first pre-impregnated material and the second pre-impregnated material at the curing temperature so that the second pre-impregnated material adheres to the first pre-impregnated material. Additional layers may be added to the layered material as well.

As shown in FIG. 6, the backing paper 102 is shown sandwiched between layers 112 and 120 of the layered material 118. When the layered material 118 is cured, the encapsulated blowing agent 110 is activated, thereby creating one or more voids 122 in the layered material 118. In such an example, analyzing signals indicative of the ultrasonic waves to determine at least one property of the cured pre-impregnated material comprises detecting the one or more voids in the layered material to thereby determine that at least a portion of the backing paper is sandwiched between the pre-impregnated material and the second material. Once detected, the computing device may determine whether a repair is needed. In one example, the computing device may determine a size, depth, and or location of the detected backing paper to determine whether to leave the FOD in the layered material, repair the layered material, or replace the layered material.

When the blowing agent 110 is activated, the internal pressure generated during the void nucleation and growth may be in the thousands of PSI. In the curing process in creating the layered material 118, the external pressure could be up to hundreds of PSI (normally up to 100 psi) in hot press curing and up to 14 psi in autoclave curing. Therefore, the foaming process cannot be suppressed by the external pressure exerted on the composite stack during curing process. As long the curing temperature is higher than the blowing agent activation temperature, any backing paper 102 left behind will create voids that are easily detected by NDE.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method comprising:
   mixing a coating material with a blowing agent such that the blowing agent is encapsulated within the coating material and uniformly dispersed throughout an entirety of the coating material, wherein the coating material comprises a silicone material, and wherein a weight of the blowing agent encapsulated in the coating material comprises between about 0.1% to about 3% of a combined weight of the blowing agent and the coating material;
   applying the coating material to a first surface of a backing paper; and
   curing the coating material at a first temperature that is less than an activation temperature of the blowing agent.

2. The method of claim 1, further comprising:
   applying the first surface of the backing paper to a first surface of an uncured pre-impregnated material, wherein the first surface of the backing paper is removably coupled to the first surface of the uncured pre-impregnated material.

3. The method of claim 2, further comprising:
removing the backing paper from the first surface of the uncured pre-impregnated material;
placing the uncured pre-impregnated material on a second material; and
curing the pre-impregnated material and the second material at a curing second temperature so that the pre-impregnated material adheres to the second material to create a layered material.

4. The method of claim 3, wherein the second temperature is above the activation temperature of the blowing agent, such that the blowing agent of any backing paper unintentionally left between the pre-impregnated material and the second material is activated when the pre-impregnated material is cured.

5. The method of claim 4, wherein curing the pre-impregnated material at the second temperature above the activation temperature of the blowing agent comprises curing the pre-impregnated material at the activation temperature of the blowing agent in a range from about 200° F. to about 450° F.

6. The method of claim 4, further comprising:
detecting one or more voids in the layered material to thereby determine that at least a portion of the backing paper is sandwiched between the pre-impregnated material and the second material.

7. The method of claim 1, wherein the blowing agent comprises a chemical blowing agent.

8. The method of claim 7, wherein the chemical blowing agent is one of azodicarbonamide, benzene sulfonyl hydrazide, toluenesulfonyl-semicarbaside, 5-Phenyltetrazole, dinitrozopentamethylentetraamin, sodium bicarbonate, or citric acid.

9. The method of claim 1, wherein the blowing agent comprises a physical blowing agent.

10. The method of claim 9, wherein the physical blowing agent is one of chlorofluorocarbons (CFCs), hydrochlorofluorocarbons (HCFCs), hydrofluorocarbon (HFC), propane, isobutane, pentane, ethanol, carbon dioxide (CO2), or nitrogen (N2).

11. The method of claim 1, wherein the blowing agent comprises a mixed physical/chemical blowing agent.

12. The method of claim 2, further comprising:
rolling the backing paper and the uncured pre-impregnated material simultaneously such that a second surface of the uncured pre-impregnated material contacts a second surface of the backing paper such that the second surface of the backing paper is removably coupled to the second surface of the uncured pre-impregnated material.

13. The method of claim 12, further comprising:
unrolling the backing paper and the uncured pre-impregnated material such that the second surface of the backing paper is removed from the second surface of the uncured pre-impregnated material prior to removing the backing paper from the first surface of the uncured pre-impregnated material.

14. The method of claim 6, wherein detecting one or more voids in the layered material comprises:
positioning the layered material in a field of view of a transducer;
generating, using the transducer, a plurality of ultrasonic waves;
receiving ultrasonic waves reflected from and generated in the layered material; and
analyzing, using a computing device, signals indicative of the ultrasonic waves to thereby detect the one or more voids in the layered material.

15. The method of claim 14, further comprising:
directing the ultrasonic waves emitted by the transducer at a surface of the layered material.

16. The method of claim 2, wherein the uncured pre-impregnated material is a first uncured pre-impregnated material, the method further comprising:
placing a second uncured pre-impregnated material on the first uncured pre-impregnated material; and
curing the first pre-impregnated material and the second pre-impregnated material at the curing temperature so that the second pre-impregnated material adheres to the first pre-impregnated material.

17. The method of claim 1, wherein the blowing agent comprises a particle into which the blowing agent is positioned.

18. The method of claim 17, wherein the particle have a size ranging from about 3 μm to about 50 μm.

19. The method of claim 1, wherein the backing paper comprises an uncoated plastic film, and wherein the blowing agent is mixed into the uncoated plastic film during a film extrusion process such that the blowing agent is uniformly dispersed in the backing paper both in plane and in thickness.

20. The method of claim 1, wherein the backing paper comprises a cellulose paper, a polymeric sheet including polyamide, a polyether-terephthalate, a polyethersulphones, an acrylate polymer, a polyester, a polyethylene, or copolymers thereof.

* * * * *